(12) United States Patent
Flynn

(10) Patent No.: US 11,136,543 B1
(45) Date of Patent: Oct. 5, 2021

(54) MAGNETIC CELL INCUBATION DEVICE

(71) Applicant: Edward R. Flynn, Peoria, AZ (US)

(72) Inventor: Edward R. Flynn, Peoria, AZ (US)

(*) Notice: Subject to any disclaimer, the term of this patent is extended or adjusted under 35 U.S.C. 154(b) by 0 days.

(21) Appl. No.: 17/023,084

(22) Filed: Sep. 16, 2020

Related U.S. Application Data

(60) Provisional application No. 62/972,873, filed on Feb. 11, 2020.

(51) Int. Cl.
*C12M 1/34* (2006.01)
*G01N 35/00* (2006.01)
*A61B 5/0515* (2021.01)
*G01N 27/72* (2006.01)

(52) U.S. Cl.
CPC .......... *C12M 41/46* (2013.01); *A61B 5/0515* (2013.01); *G01N 27/72* (2013.01); *G01N 35/0098* (2013.01)

(58) Field of Classification Search
CPC ....... G01N 27/72; A61B 5/0515; C12M 41/46
See application file for complete search history.

(56) References Cited

U.S. PATENT DOCUMENTS

| | | | |
|---|---|---|---|
| 4,018,886 A | 4/1977 | Giaever | |
| 4,442,404 A | 4/1984 | Bergmann | |
| 4,590,922 A | 5/1986 | Gordon | |
| 4,675,286 A | 6/1987 | Calenoff | |
| 4,735,796 A | 4/1988 | Gordon | |
| 4,829,984 A | 5/1989 | Gordon | |
| 4,859,610 A | 8/1989 | Maggio | |
| 4,950,221 A | 8/1990 | Gordon | |
| 4,962,023 A | 10/1990 | Todd et al. | |
| 5,043,101 A | 8/1991 | Gordon | |
| 5,384,109 A | 1/1995 | Klaveness et al. | |
| 5,496,534 A | 3/1996 | Klaveness et al. | |
| 5,506,500 A | 4/1996 | Krause et al. | |
| 5,735,279 A | 4/1998 | Klaveness et al. | |
| 5,759,793 A | 6/1998 | Schwartz et al. | |
| 5,827,478 A | 10/1998 | Carey et al. | |
| 5,921,244 A | 7/1999 | Chen et al. | |
| 5,928,535 A | 7/1999 | Trinkner et al. | |
| 6,203,487 B1 | 3/2001 | Consigny | |
| 6,470,220 B1 | 10/2002 | Kraus | |
| 6,485,985 B1 | 11/2002 | Weitschies | |
| 6,739,342 B1 | 5/2004 | Fredricksson et al. | |
| 6,997,863 B2 | 2/2006 | Handy et al. | |

(Continued)

OTHER PUBLICATIONS

Guedes et al., "Hybrid GMR Sensor Detecting 950 pT/sqrt(Hz) at 1 Hz and Room Temperature", 2018, Sensors, 18, 790, pp. 1-8. (Year: 2018).*

(Continued)

*Primary Examiner* — Jonathan M Hurst
(74) *Attorney, Agent, or Firm* — Peacock Law P.C.; Janeen Vilven

(57) ABSTRACT

A compact device for measuring incubation of living cells with molecules attached to superparamagnetic nanoparticles consisting of iron cores by magnetizing the nanoparticles with an external pulsed field, measuring the time dependence of decaying magnetic fields of the nanoparticles as they attach to the cells by a magnetic sensor, extracting number of attached nanoparticles per cell and rate of incubation by mathematical analysis of the magnetic field emitted by the incubating cells versus time.

22 Claims, 15 Drawing Sheets

(56) References Cited

U.S. PATENT DOCUMENTS

| | | | |
|---|---|---|---|
| 7,074,175 | B2 | 7/2006 | Handy et al. |
| 7,217,391 | B2 | 5/2007 | Gjerdingen et al. |
| 7,309,316 | B1 | 12/2007 | Flynn et al. |
| 7,452,662 | B2 | 11/2008 | Dupuis et al. |
| 7,459,145 | B2 | 12/2008 | Bao et al. |
| 7,662,632 | B2 | 2/2010 | Franco |
| 7,906,345 | B2 | 3/2011 | Wang et al. |
| 8,060,179 | B1 | 11/2011 | Flynn |
| 8,323,957 | B2 | 12/2012 | Bartsch |
| 8,394,339 | B2 | 3/2013 | Silverbrook et al. |
| 8,447,379 | B2 | 5/2013 | Flynn |
| 8,834,381 | B2 | 9/2014 | Clemmons et al. |
| 8,947,518 | B2 | 2/2015 | Kiyota et al. |
| 9,074,976 | B2 | 7/2015 | Adolphi et al. |
| 9,081,007 | B2 | 7/2015 | Pollack et al. |
| 9,095,270 | B2 | 8/2015 | Flynn |
| 9,395,361 | B2 | 7/2016 | Pamula et al. |
| 9,404,074 | B2 | 8/2016 | Kiyota |
| 9,428,723 | B2 | 8/2016 | Lee et al. |
| 10,031,132 | B2 | 7/2018 | Foppen et al. |
| 10,233,481 | B2 | 3/2019 | Marshall et al. |
| 2017/0067969 | A1* | 3/2017 | Butters ............... G01R 33/032 |

OTHER PUBLICATIONS

Adolphi, Natalie L. et al., "Characterization of magnetite nanoparticles for SQUID-relaxometry and magnetic needle biopsy", Journal of Magnetism and Magnetic Materials, vol. 321, 2009, 1459-1464.

Adolphi, Natalie L., et al., "Characterization of Single-core Magnetite Nanoparticles for Magnetic Imaging by SQUID-relaxometry", Submitted to IOP Publishing for peer review, 2010, 1-27.

Adolphi, Natalie L., et al., "Imaging of Her2-Targeted Magnetic Nanoparticles for Breast Cancer Detection: Comparison of SQUID-detected Magnetic Relaxometry and MRI", Contrast Media Mol Imaging., vol. 7, No. 3, 2012, 1-25.

Bryant, H. C., et al., "Magnetic properties of nanoparticles useful for SQUID relaxometry in biomedical applications", Journal of Magnetism and Magnetic Materials, vol. 323, Issue 6, 2011, 767-774.

Butler, Kimberly S., et al., "Development of Antibody-Tagged Nanoparticles for Detection of Transplant Rejection Using Biomagnetic Sensors", Cell Transplantation, vol. 22, 2013, 1943-1954.

Chemla, Y. R., et al., "Ultrasensitive magnetic biosensor for homogeneous immunoassay", PNAS, vol. 97, No. 26, 2000, 14268-14272.

De Haro, Leyma P., et al., "Magnetic relaxometry as applied to sensitive cancer detection and localization", Biomed. Eng.-Biomed. Tech., 2015, 1-11.

Espy, M. A., et al., "Two Methods for a first order hardware gradiometer using two high temperature superconducting quantum interference devices", Rev. Sci. Instrum., vol. 69, No. 1, 1998, 123-129.

Flynn, E. R., et al., "A Biomagnetic System for in vivo Cancer Imaging", Phys. Med. Biol., vol. 50, 2005, 1273-1293.

Flynn, Edward R., et al., "Use of a SQUID Array to Detect T-Cells with Magnetic Nanoparticles in Determining Transplant Rejection", Journal of Magnetism and Magnetic Materials, vol. 311, 2007, 429-435.

Grossman, H. L., et al., "Detection of bacteria in suspension by using a superconducting quantum interference device", PNAS, vol. 101, No. 1, 2004, 129-134.

Hathaway, Helen J., et al., "Detection of breast cancer cells using targeted magnetic nanoparticles and ultra-sensitive magnetic field sensors", Breast Cancer Research, vol. 13, No. R108, 2011, 1-13.

Jaetao, Jason E., et al., "Enhanced Leukemia Cell Detection Using a Novel Magnetic Needle and Nanoparticles", Cancer Res, vol. 69, No. 21, 2009, 8310-8316.

Johnson, Cort, et al., "Magnetic relaxometry with an atomic magnetometer and SQUID sensors on targeted cancer cells", Journal of Magnetism and Magnetic Materials, vol. 324, 2012, 2613-2619.

* cited by examiner

Rate Equation

$$\frac{d\rho}{dt} = \alpha\,(\rho_{so} - \rho)(\rho_{no} - \rho)$$

Solution to Rate Equation $$\rho(t) = \frac{\rho_{so}\{e^{-\alpha \rho_{no}(\rho_{so}/\rho_{no} - 1)t} - 1\}}{e^{-\alpha \rho_{no}(\rho_{so}/\rho_{no} - 1)t} - \rho_{so}/\rho_{no}}$$

FIG. 6

Incubation Study of Prostate Cells

| Input and Results of Fits: | | | | | |
|---|---|---|---|---|---|
| From 10 micl Cotton Tip (See Notes in Logbook) | | | | M | 1.68E+05 |
| Amount of np Solution | | | | micl | 8.00E+01 |
| mg/ml of Ocean 1015SS 30 nm Carboxyl with | | | | mg/ml | 6.77E+00 |
| mg/ml of Ocean 1015SS 30 nm Carboxyl with | | | | mg/ml | 1.05E+01 |
| Weight of One np | | | | mg/np | 3.79E-14 |
| Number of np in 80 micl PSMA Solution | | | | #np | 1.43E+13 |
| Number of np in micl BSA Solution | | | | #np | 2.22E+13 |
| Moment/np (PSMA) on 10 micl Tip | | | | M/np | 9.41E-08 |
| Number of Cells | | | | #cells | 3.00E+06 |
| Number of Sites/Cell | | | | | |
| | LnCAP | PSMA | | sites/cell | 6.67E+06 |
| | LnCAP | BSA | | sites/cell | 4.24E+05 |
| | C4-2 | PSMA | | sites/cell | 5.98E+06 |
| | C4-2 | BSA | | sites/cell | 5.17E+05 |
| R (PSMA/BSA) | | LnCAP | ## | 11.57 | |
| Rate | Consider | (1e-13)*a0=a / #np | | | |
| | LnCAP | PSMA | | a[per min] | 0.591 |
| | LnCAP | BSA | | a[per min] | 0.541 |
| | C4-2 | PSMA | | a[per min] | 1.403 |
| | C4-2 | BSA | | a[per min] | 1.203 |

FIG. 9
(Continued)

HTC Squid (TristanTech)
Sensitivity < 70 fT/cm/√Hz
Operating temp 77 K (Liquid Nitrogen)
Gradiometer Baseline=10 mm
Pickup Coil 8mm x 8mm
Field Range 0 -> 1mT Atomic Magnetometer (TwinLeaf)
Sensitivity 200 fT/√Hz
Sensor Size = 1.6(d) x 15 (l) cm
Power 2.5 W
Field Range +/- 100 nT

MAGNETIC CELL INCUBATION DEVICE

CROSS-REFERENCE TO RELATED APPLICATIONS

This application claims priority to and the benefit of the filing of U.S. Provisional Patent Application No. 62/972,873, entitled "A Magnetic Cell Incubation Device", filed on Feb. 11, 2020, and the specification and claims thereof are incorporated herein by reference.

BACKGROUND

The present invention relates generally to methods and apparatus for incubating cells with various molecules attached to superparamagnetic nanoparticles when in their presence such as cancer cells with specific antibodies. Medical applications of this type of incubation include determination of cancer cell type and of appropriate antibodies or chemical agents for treating cancer.

A number of methods are currently used for incubation. They generally involve a series of steps of adding the molecules to the cells and then performing biochemical measurements to determine if the molecules have attached to the cells during the incubation process. The methods are complex, yield limited quantitative information on the actual number attached to the cells and the rate of the attachment, the rate being important for determining time of response to adding various molecules to cells in vivo or in vitro.

Incubation technology has not changed for several decades and the methodology has remained essentially unchanged. In these current applications there is no way of determining the exact number of antibodies that attach to the cells and limited methods of measuring the relative specificity of antibodies for cells. Determination of the rate that incubation occurs is limited in existing methods. The ability to adequately measure the resulting number of molecules attached to the cells following incubation is confounded by two major considerations: 1.) The biochemistry of the process, and 2.) the sensitivity of the method to the number of agents on the cells. The present invention is the exception through the use of magnetic nanoparticles with antibodies that are used to select certain cells during the incubation process by magnetic means.

The number of molecules and the rate of attachment can be of importance in numerous applications. One example is the incubation of cancer cells with antibodies specific to certain types of cancer. The measurement of the number of antibodies attaching to the cells during the incubation is a measure of the specificity of that antibody for that cancer cell, the rate of attachment determines how fast that antibody will be effective when added to the cells in vivo or in vitro. The higher the specificity the greater the definition of the cancer type and the more effective that antibody will be as a treatment for that cancer.

Breast cancer is an example of a common malignancy. There are a number of variables that can be used to assess a patients' prognosis and thus tailor therapy. These include the measurement of the specificity of different antibodies for the cancer cells present in the tumor. Cells obtained in biopsies of tumors can be incubated with antibodies to determine both the type of breast cancer as well as the most appropriate method for treatment. A more efficient and quantitative incubation method will increase determination of the most effective antibody resulting in a better prognosis and course of action. [Hathaway et al, Adolphi et al]

Patients with various forms of leukemia, lymphoma and myeloma are treated with autologous hematopoietic stem cell transplants (HSCT). In this procedure, hematopoietic stem cells (HSC) are isolated from the patient and may be tested for the most effective treatment by determining the appropriate antibody through highly sensitive incubation methods. The current invention is applicable both before and after treatment by measuring the number of antibodies present in the cell sample to determine if the cancer cells have been eradicated, a measurement of minimal disease. [Jaetao et al].

Advances in the staging of various solid tumors has been led by the advent of CAT scans and more recently PET scans. Patients with a localized tumor often are found to have a small suspicious nodule in a metastatic site and confirmation is required to determine if these metastatic nodules are malignant for decisions on the correct treatment. It is currently routine clinical practice to biopsy these lesions, often by a CAT scan guided needle biopsy. The current invention will determine if the biopsy is benign and if cancer, the cancer type through determination of the type of antibody that attaches to it through incubation of the biopsy sample with the antibodies conjugated to magnetic nanoparticles.

There is a large range of antibodies known for numerous cancer types such as leukemia, breast, prostate, and Hodgkin's disease. There are also known neo-vascular agents, toxins and chemicals that can be attached to magnetic nanoparticles for seeking out tumors and delivering compounds that will cause harm to cancer cells.

The device described here utilizes the special properties of magnetic nanoparticles in the size range of tens of nanometers. These are conjugated to the chemical agents, e.g. antibodies, and the special properties of these nanoparticles are used to determine the number of molecules/cell and the rate of cell attachment. [Bryant et al, Flynn et al De Haro et al].

The use of magnetic nanoparticles with appropriately-labeled antibodies to target certain specific types of cancer, drug separation and the use of RF heating of magnetic particles for hyperthermia treatment is known (U.S. Pat. Nos. 5,735,279; 5,738,837; 5,043,101; 6,459,924; 5,067,952; 5,203,782; and Proceedings of the Scientific and Clinical Applications of Magnetic Carriers (Hafeli, Urs, Schutt, W., Teller, J., Zborowski, M., (eds.), Plenum Press, N Y, 1997; Hafeli, U., Zbrowoski, M., (Eds.) J. Magn. Magn. Mater. 194, 1999; Hafeli, U., Zbrowoski, M., (Eds.), J. Magn. Magn. Mater. 225, 2001). See also Flynn references. The use of antibodies to target certain cells during incubation is known (U.S. Pat. Nos. 10,233,481, 10,031,132, 9,395,361, 9,081,007, 8,846,410, 8,637,324.

The present invention has an advantage over systems and methods previously disclosed in that they do not measure the number of cells attached during the incubation process nor do they have the capability of directly measuring the rate of attachment. Chemia et al have demonstrated that magnetic nanoparticles conjugated to antibodies can be used to identify cell types in a homogeneous immunoassay experiment where they take advantage of the difference between bound and unbound decay of nanoparticles with a SQUID measurement system. However, this is not an incubation experiment, no attempt was made to determine the rate of incubation or the number of antibodies attached to the cells.

The magnetic nanoparticles of primary interest in this invention are superparamagnetic rather than ferromagnetic providing the important advantages of not attracting each other to form agglomerates when not in the presence of an external field. Superparamagnetic particles exhibit paramagnetic properties in the absence of a magnetic field but have ferromagnetic properties when in the presence of such fields, exhibiting susceptibilities of many thousands. This phenomenon occurs when the external magnetic field polarizes all of the particles along the field lines. When the polarizing field is turned off, the particles momentarily exhibit a collective dipolar magnetic moment which then decays with a time. The rate of decay is determined by the size of the particles and whether the particles are bound to some substance. An example of such binding is with a cell through the attachment of the particle conjugated to an antibody specific to the cell. The magnitude of this decaying magnetic field from cells incubated with antibody-nanoparticles (np+Ab) depends upon the magnetic dipolar moment of the cell sample. The dipolar moment is determined by the number of np+Ab attached to the cells and the magnetic moment of an individual nanoparticle.

The rate of attachment is determined by making such magnetic field measurements as a function of time after adding the conjugated nanoparticles and molecules to the cells until saturation occurs indicating that all available sites on the cells are now occupied by molecules. A mathematical fit to the data as a function of time yields the final number of molecules attached to a known number of cells. Quantitative information on chemical methods for measuring incubation is limited and more time consuming than the present invention.

BRIEF SUMMARY OF THE INVENTION

According to one embodiment of the present invention, a molecule is conjugated to superparamagnetic nanoparticles then introduced into a vial (e.g. a 1.5 mL Eppendorf tube) containing a known number of cells for incubation. The vial is inserted into a compact (approximately 20 cm in diameter by 20 cm high) magnetically shielded measurement chamber. A magnetizing field is applied for a fraction of a second followed by measurement of the induced magnetic field of the nanoparticles-molecules as they attach to the cells using a magnetic sensor. The process is repeated at fixed intervals until the measured magnetic signal reaches a maximum. A mathematical fit to the resulting magnetization versus time data determines the number of molecules attached to each cell and the rate of attachment.

In another embodiment of the present invention, the cells are cancer cells and the molecules are an antibody for cancer, the resulting measurement produces the specificity of the antibody for the cancer cell type.

In another embodiment of the present invention, the cells are cancer cells, the molecule is an anticancer drug such as a chemotherapy drug and the resulting incubation measurement determines the effect of that particular chemotherapy for that cancer cell.

In another embodiment of the present invention, the cells and np+Ab are placed in the incubation device, during the incubation process, a second molecule is introduced and the incubation process continued, the result of the measurement determining the capability of the second molecule to effect the first molecule on the cells such as stripping the first molecule from the cells.

One aspect of the present invention is an accurate measurement of the specificity of the molecule for attachment to the cells present by measuring the number of molecules, such as antibodies, that attach to the cells, such as cancer cells. Measurement of specificity using various antibodies is used for determining the type of cancer.

Another aspect of the present invention using the previous aspect is used to determine the most specific antibody for a particular type of cancer.

Another aspect of the present invention is the determination of the rate that chemical agents, such as antibodies, attach to the cells, such as cancer cells, present in order to know how fast to expect the incubation to occur during in-vivo experiments on animals or humans.

Another aspect of the present invention is to measure the properties of unknown superparamagnetic nanoparticles for magnetic relaxometry applications by comparing such particles to known nanoparticles in incubation studies with known cells and antibodies.

Another aspect of the present invention is to measure the effectiveness of various processes for biochemical conjugation of molecules and magnetic nanoparticles

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more embodiments of the invention and are not to be construed as limiting the invention. In the drawings:

FIG. 6 is the rate equation describing the rate of change of magnetic moment as a function of time following addition of the cells to the np+Ab. $\rho$ is the density of np+Ab bound to cells, $\rho_{so}$ is the number of available sites on the cell and $p_{no}$ is the number of available np's. The lower equation is the result of integration of the rate equation.

DETAILED DESCRIPTION OF THE INVENTION

According to an embodiment of the present invention a magnetic cell incubation device consists of a sample holder for adding cells to superparamagnetic np attached to specific molecules, a Helmholtz magnetizing coil for magnetizing the samples and a magnetic sensor to measure the magnetic fields emitted by the nanoparticles subsequent to the magnetization step. The method is called superparamagnetic relaxometry (SPMR). The device consists of a compact magnetically shielded chamber (approximately twenty cm in diameter and 20 cm in height) designed to fit on a laboratory bench (typically 50 cm deep by 100 cm wide) requires less than one hundred watts of power for any incubation measurement. Measuring sequences and magnetic measurements are automated through a computer interface with incubation results displayed in real time.

Figure 1:
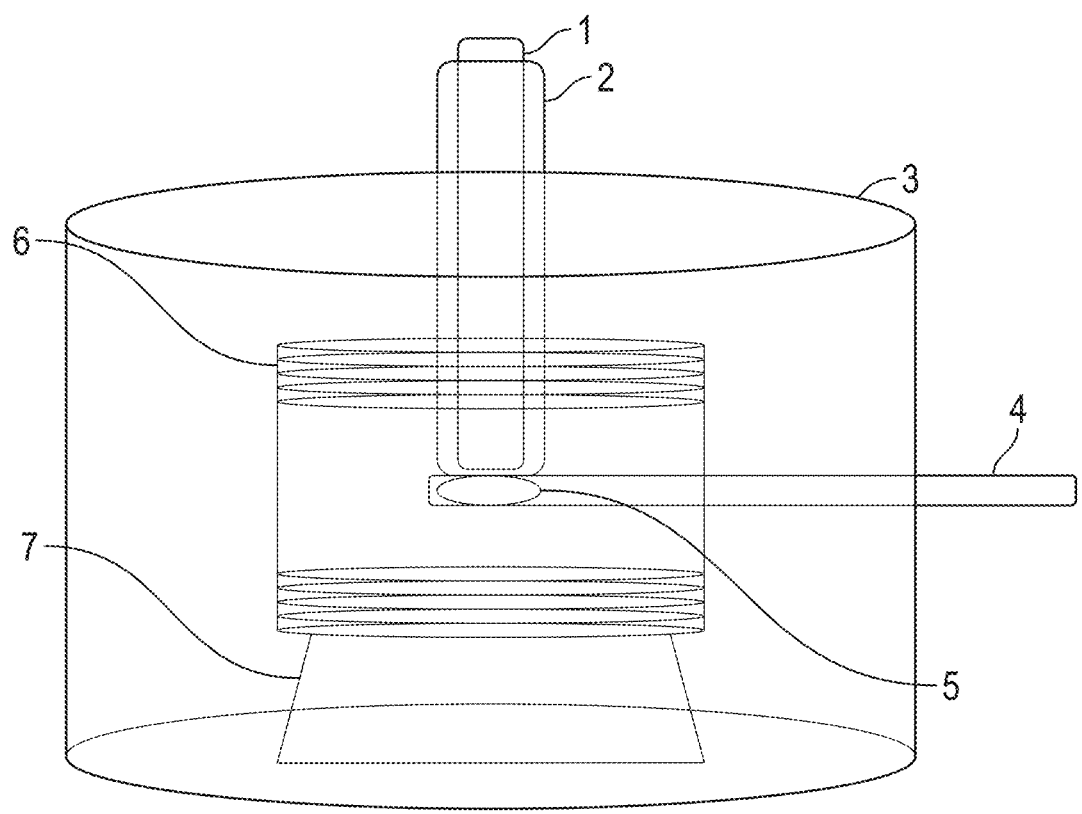
FIG. 1 is a conceptual drawing of the present invention consisting of an enclosure, which may consist of magnetically shielding metal, a sample holder, a Helmholtz magnetizing coil and a single magnetic sensor. The size of the device is approximately 20 cm in diameter by 20 cm in height excluding the height of the magnetic sensor chosen.

The embodiment of the present invention is shown in FIG. 1. A typical procedure for an incubation measurement is: (a) molecules conjugated to nanoparticles are inserted into small vials, e.g. Eppendorf tubes 2 mL volume or less; (b) The vial is inserted into the Cell Sample Chamber. (c) A SPMR measurement of the sample is made to establish a background field. (d) The vial is extracted, cells are added, and the vial is immediately reinserted into the Cell Sample Chamber. (e) SPMR measurements are made as a function of time by pulsing the Helmholtz magnetization coils. (f) Each SPMR measurement is fit to an analytical expression to extract the magnetic field decay magnitude, the magnitudes are plotted as a function of each time point, and the resulting data of field vs time is fit to an algorithm to extract the final number of incubated molecules per cell and the rate of incubation.

The measurement chamber [3] consists of a magnetically shielding material approximately twenty cm in size and twenty cm in height containing the sample holder insertion tube [4], a Helmholtz magnetizing coil [6a and 6b] and support [7], and the magnetic field sensor tube [2] emerging from the top of the assembly. The sample containing the nanoparticles plus molecules [5] is inserted into the sample holder insertion tube for measurements. The decaying magnetic fields induced into the sample by the SPMR process are measured by a magnetic field sensor [1] located in the sensor insertion tube.

A typical SPMR measurement is carried out in the following manner. A magnetizing pulse length is applied to the sample for 0.75 sec, or of similar time depending on sample parameters. The decaying magnetic field of the np+Ab (or other molecules) as they bind to the cells following the magnetizing pulse is measured by a magnetic field sensor located above the sample. The pulse is applied at fixed intervals determined by the expected incubation rate (measurements may vary from 3 to 180 sec intervals). Normally a total time of 900 seconds is sufficient to achieve saturation of the sample where all sites on the cells are occupied.

Different magnetic sensors may be used interchangeably in this embodiment depending on the sensitivity required during the incubation measurement. The compact device design permits the sensor face to be located two mm from the sample eliminating the need for ultrasensitive sensors that require liquid helium. Multiple sensor types exist that are compatible with this design as well as future sensor types under development at various companies.

In a typical device, the measurement chamber is a cylinder of high magnetic permeability metal for shielding from external fields, multiple concentric layers of shielding material may be added for increased shielding. The sample and sensor extension tubes also consist of this same material in the sections that extend outside of the measurement chamber. External magnetic coils around the chamber may also be used to provide further shielding through ceiling out external environmental fields.

The magnetizing coil to magnetize the nanoparticles are in a circular Helmholtz arrangement with two coils separated by half the diameter of the coils. They are located above and below the vial containing the sample. In the embodiment of this invention, the coils are approximately ten cm in diameter separated by 5 cm. The coil windings are chosen to each have 50 turns of #20 wire in each coil. A current of 5.0 A is applied during the pulse, requiring a milliwatt power supply. producing a magnetic field at the center of 75 Gauss (0.0075 T). Other combinations of number of turns, size of wire, and current may also be used to achieve the same result. The coils as shown are for magnetic sensors that measure in the direction perpendicular to the sensor face. For sensors that measure fields parallel to their face, the magnetizing coils would be rotated 90 degrees. Other configurations of magnetizing coils, sensor positions and measurement chamber may also be used for SPMR measurements within this measurement chamber.

During the process of developing SPMR procedures for animal experiments on this instrument, a new method for incubation of molecules and cells was discovered. This discovery involved the incubation of cells with antibodies (Ab) conjugated with superparamagnetic nanoparticles (np). The cells were of various cancer types used to produce cancerous tumors in the animals and the antibodies were specific to these cancer types. Before injection into animals, cells were incubated with the np+Ab in Eppendorf tubes while subjected to SPMR procedures to see if the Ab were specific to the cells. The results of these experiments provided the data for the basis of the invention of a dedicated desktop magnetic incubation device presented here.

Figure 2:
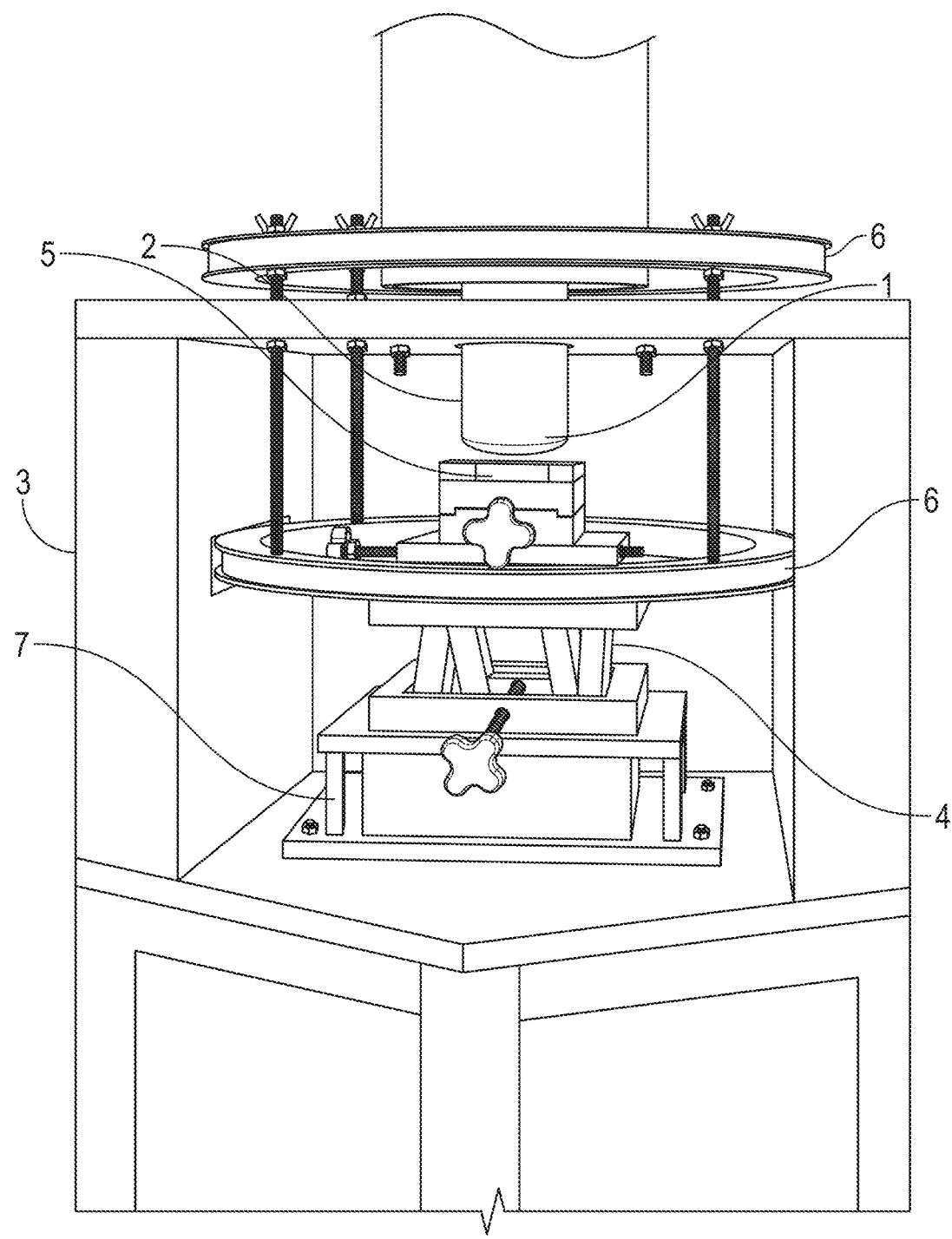
FIG. 2 is a photograph of an instrument used for superparamagnetic relaxometry (SPMR) measurements to detect and localize cancer in animals and humans.

The instrument shown in FIG. 2 is one embodiment for detecting and locating cancer in animals (and eventually humans) using the SPMR methodology. It contains an array of superconducting sensors [1], a 35 A current magnetizing coil [6] and a stage [4] for moving small animals [5] under the sensor system [7] in order to map emitted fields from the animal under investigation. The instrument [3] is approximately three meters high by one meter in diameter with 1.2 meter magnetization coils and seven superconducting quantum interference (SQUID) magnetic sensors. A seven sensor low temperature SQUID system [2] requiring seven liters of liquid helium is required in order to map and localize np sources in animals. The instrument has a value of approximately $300,000. This system relies on the use of liquid helium to achieve the desired sensitivity because of the geometry required to measure tumors in mice and map their locations. Liquid helium is becoming increasingly difficult to obtain, is very expensive, and requires trained technicians to transfer. This instrument utilizes large Helmholtz magnetization coils one meter in size requiring a current of 30 A and a power supply of 3.5 KW to produce a magnetizing field of 33 Gauss. The size of the system shown in FIG. 2 would require a large magnetically shielded room to reduce external environmental magnetic fields. Such rooms cost close to one million dollars to build. The performance of this system is limited by the presence of such external fields rather than the sensitivity of the sensor system consisting of low-temperature SQUIDS.

The embodiment of the invention as illustrated in FIG. 1 is based on the discovery of novel incubation procedures during development of the animal SPMR system. The current invention will cost less than a tenth of the system shown in FIG. 2 and will be of a size that it can reside on a standard laboratory countertop and is portable via hand carry by one or two individuals. A power supply only one percent of the large system is required for magnetization coils. Only a single magnetic field sensor is required as incubation measurements do not necessitate mapping that needs multiple spatial magnetic measurements. The invention configuration is such that high sensitivity sensors requiring liquid helium are not necessary.

Figure 3:
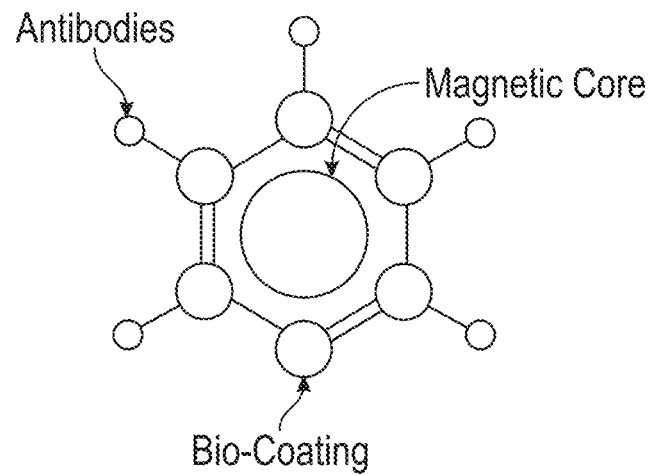
FIG. 3 is a graphical illustration of a magnetic nanoparticle which contains a superparamagnetic core, a coating of a biocompatible material, and a coating of chemical agents such as specific antibodies. A magnetic dipole direction occurs when magnetized according to one embodiment of the present invention.

The invention described here, is also a Superparamagnetic Relaxometry (SPMR) device and as such, requires the use of superparamagnetic nanoparticles (np) to function. In the embodiment of the invention, the SPMR method measures the relaxation rate of superparamagnetic np following a pulse of magnetizing field. The np are superparamagnetic and do not form clusters when not in the presence of an external magnetic field. The np used in this invention contain a central core of superparamagnetic material with a diameter of 10 to 50 nm, typically consisting of iron oxide as shown in FIG. 3. Surrounding this core is a coating compatible with conjugating the molecule of interest to the np. In the illustration shown, the molecules are antibodies although other types of molecules may also be used. A number of companies supply these np in the size range needed for these measurements, ~25 nm. (Ocean Nanotech (San Diego), Chemicell (Berlin), and Imagion Biotech (San Diego) are examples).

The present invention may also be used to measure np properties of untested nanoparticles for SPMR application by measuring their magnetic characteristics as a function of applied field and by comparing incubation results of new np to known np with known cells and molecules. Such measurements can be used in development of new np for Good Manufacturing Process and Good Laboratory Process required for FDA approval for SPMR clinical application.

The present invention may also be used to optimize conjugation methods of np with various molecules.

Figure 4A:
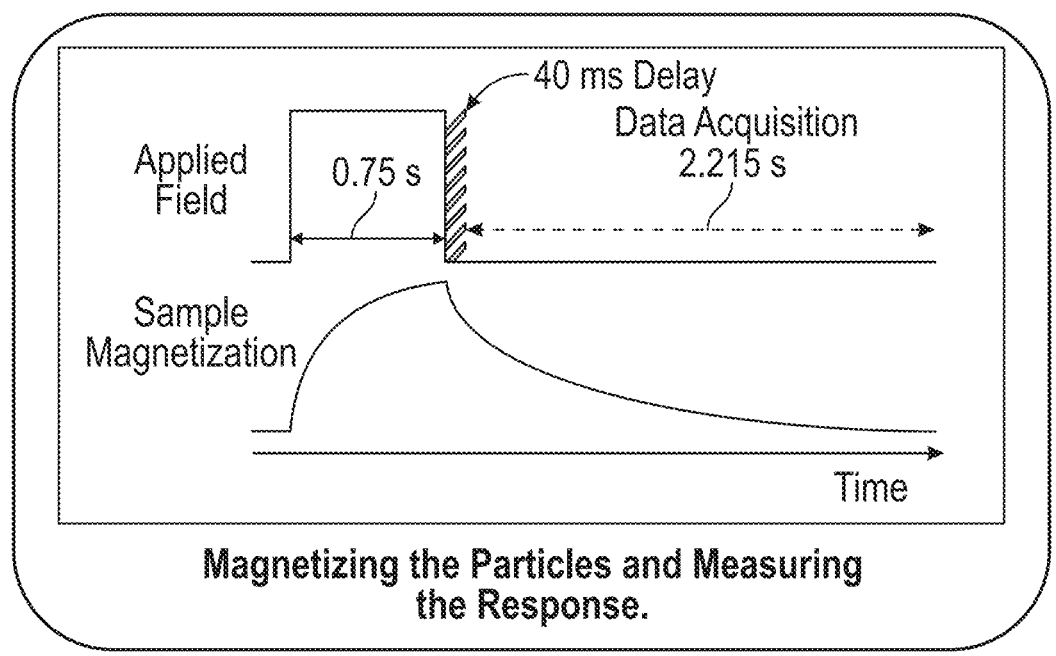
FIG. 4A-4C is described as (4A) is a graphical representation of an applied magnetizing pulse followed by the magnetic decay of a superparamagnetic nanoparticle. (4B) is the measured magnetic decay of a superparamagnetic nanoparticle when bound to a cell and when unbound. (4C) is a graphical representation of a superparamagnetic nanoparticle decaying by Brownian motion when unbound compared to a bound superparamagnetic nanoparticle bound to a cell decaying by the Neel mechanism.
Figure 4B:
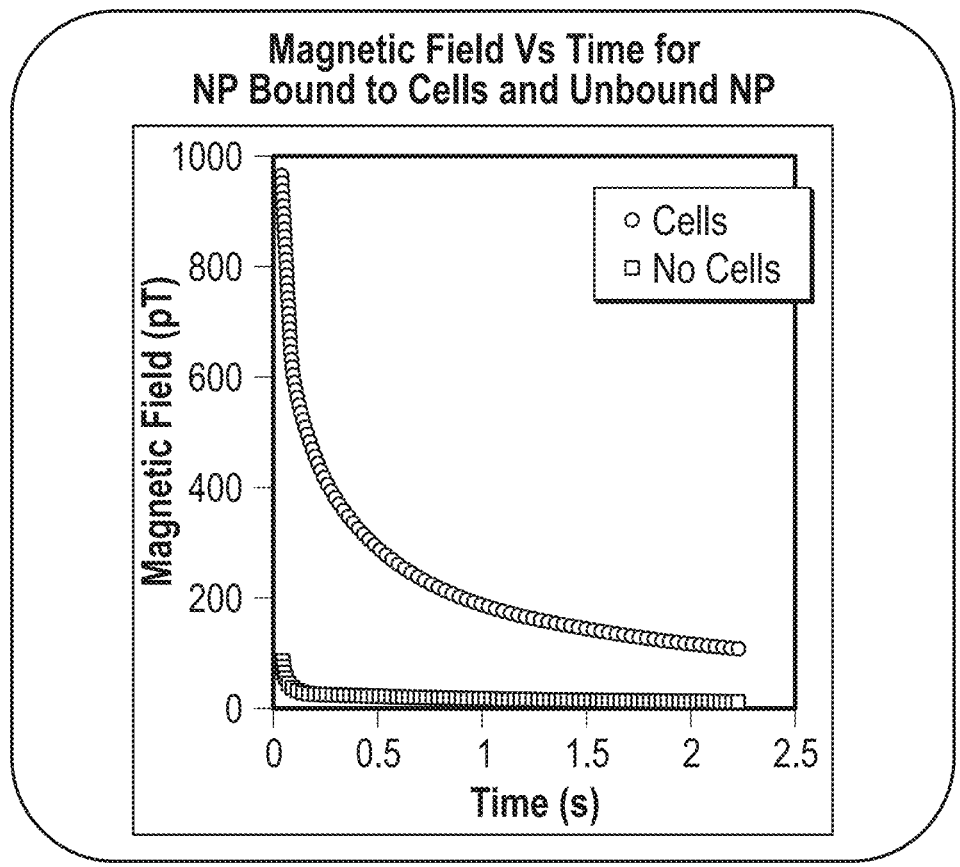
Figure 4C:
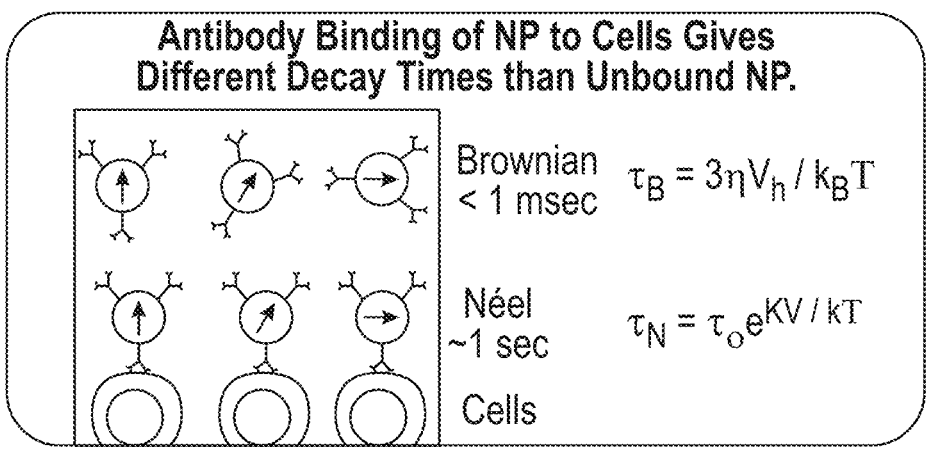

SPMR measurements require exposure to magnetic fields in order polarize the particles along the field lines. This is illustrated in FIG. 4A where the nanoparticles are subjected to a magnetizing field of approximately 40 Gauss for 0.75 sec in the system shown in FIG. 2. When the polarizing field is turned off, the particles exhibit a collective dipolar magnetic moment which decays with a time determined by the size of the particles and whether the np are bound to some object (hindered) or free to rotate (unhindered). In FIG. 4a this decay time is measured over a period of 2.215 sec following a 40 msec delay to allow the system to stabilize following the pulsing. The magnitude of the decaying field is a measurement of the effective dipolar magnetic moment of the magnetized np. If the particles are bound through the attachment of the np plus molecule to the cell, the decay time is substantially slower than the free, unhindered case. This is shown in FIG. 4B following a magnetizing pulse where the np were bound to cells by Ab interaction in the top curve of this figure whereas the lower curve shows np that are unbound and decay by Brownian motion too quickly to be measured as shown in FIG. 4C.

In the present invention, similar pulsing procedures will be performed with magnetizing fields of up to 100 Gauss producing twice the signal obtained from the system shown in FIG. 2 which is limited by power restrictions. The sample in the present invention will be close to the sensor; also increasing the magnetic signal as the magnetic field of the np is a function of the distance cubed between source and sensor. The system in FIG. 2 is restricted in distance between sensor surface and the sample due to the need for multiple sensors needed for mapping capability and the requirement that an animal can be placed under the sensors. Because of these features in the present invention, a number of other sensor types can replace the low temperature SQUID sensors.

In the embodiment of this invention, only np bound to cells produce measurable signals in the time frame of the measurements. When the incubation process begins, all of the np are present but give no signal as they have not yet begun to bind to cells. As the binding begins, the measured magnetic fields increase as the bound np produce measurable signals. When incubation is complete, i.e., all possible sites on the cells are occupied by the targeting molecules, the signal saturates. The remaining np in the sample do not contribute to this signal as they are not bound and there are no more sites on the cells to bind to.

Figure 5:
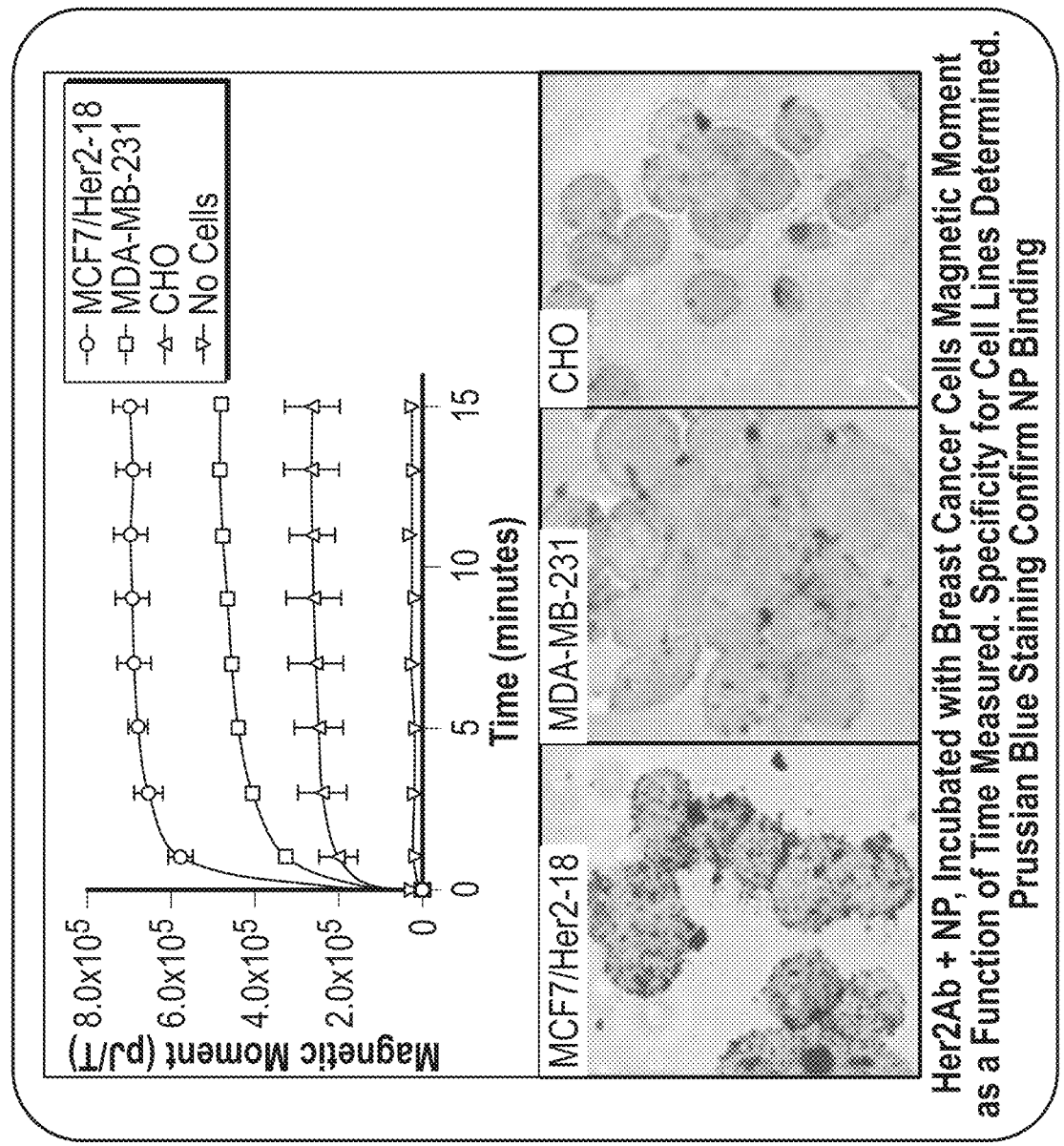
FIG. 5 The upper section contains the results of incubation of superparamagnetic nanoparticles with two human breast cancer cell lines (MCF7/Her218 and MDA-M B-23), a Chinese Hamster Ovarian (CHO); and the results of the same number of nanoparticles but no cells present. The lower section illustrates the results compared to the same cells stained by Prussian blue that shows the nanoparticles attached to cells as dark spots on the cells. [Hathaway et al].

An example of an incubation measurement that this invention will be used for is shown in FIG. 5. The graph contains data plotted as a function of the magnetic moment of the sample versus time following the addition of the cells to a solution containing the np+Ab. These incubation data were obtained by the large system shown in FIG. 2. Incubation results were obtained by a SPMR measurement applied every two minutes starting at time zero when the nanoparticles were added to the cells, ending when saturation occurs, fifteen minutes in this example. The magnitude of each curve is determined by the specificity of the Ab (Her2) for the cell type, in this case a Her2 positive human cancer cell. The magnetic moment, in given in units of pJ/T (picoJoules/Tesla). The magnetic field strength corresponding to the magnetic moment may be obtained from the known value of the magnetic moment of the np. The value of the magnetic moment of a single np is measured separately through a magnetization measurement.

The upper graph of FIG. 5 contains incubation data for two breast cancer cell lines (MCF7/Her218 and MDA-MB-231), a Chinese Hamster cell line (CHO), and no cells present. The np were conjugated to the molecule Her2 Ab. The 'no cells' present data gives the background of the system illustrating the ability of the SPMR method to discriminate against unbound np. The MCF7 cell line is highly specific to the Ab Her2/neu resulting in the largest magnetic moment, the MDA cell line being less specific. The CHO cell line measures binding for non-specific cells. The solid lines are theoretical fits to the data as described below. Qualitative verification of the incubation results is shown in the microscopic photos in the lower section of FIG. 5. Here comparisons of Prussian blue staining of the different cell lines are shown confirming the incubation measurement of specificity. These results were published in a major cancer research journal (Hathaway et al). The present invention described here will enhance this capability substantially by increased sensitivity. It will also offer low-cost and low-profile devices available to multiple institutions and industry.

Another embodiment of the present invention is the capability to make quantitative measurements of the incubation process. The equations shown in FIG. 6 have been derived to determine the number of molecules that attach to each cell during the incubation process and the rate of this attachment. Current methods of incubation lack the ability to be quantitative at this level. The top equation was derived to determine a relationship between the density of available np+Ab in solution and the density of available sites on the cells for these Ab. The differential equation gives the number of available np+Ab remaining in the sample being incubated as a function of time during the incubation. The differential equation was solved to yield the lower equation which is used to fit the data obtained in incubation measurements. Solid lines shown in previous incubation data figures are the result of fitting this equation to the data to extract information on the number of Ab attached to cells and the rate of the incubation process.

Figure 7:
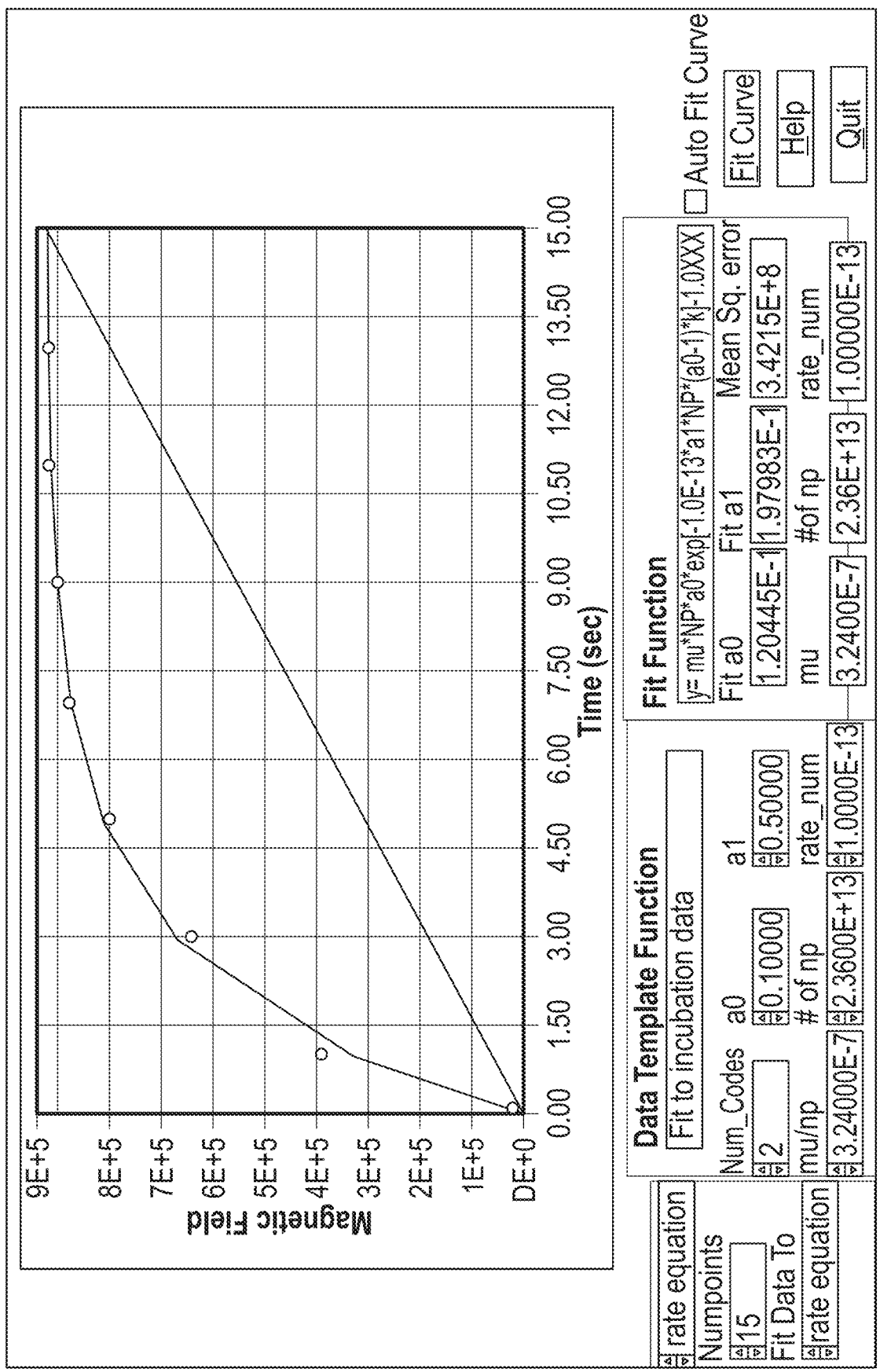
FIG. 7 is a photo of a software program that is used to fit the incubation data to the equation shown in the previous figure. The data is shown as small red dots every two minutes and the fit is the upper line. The code is a least squares code that adjusts parameters to fit the data to obtain the number of np present along with the rate.

Another embodiment of this invention is the development of computer software to obtain quantitative results to the incubation process using the paradigm represented in the equations given above. FIG. 7 is a picture of a software program that uses the solution of the rate equation to fit the data obtained during incubation. The data from one such incubation study is shown in the figure as the small crosses and the resulting fit is the upper curve shown in the graph. The fit is performed by a least-squares code using the Levenberg-Marguardt algorithm. The free parameters of the fit are the number of np+Ab attached to the cell and the rate. These are adjusted until a minimum occurs. The final values obtained provide the quantitative results to the incubation process. The software is written in both the C language and Python.

Figure 8:
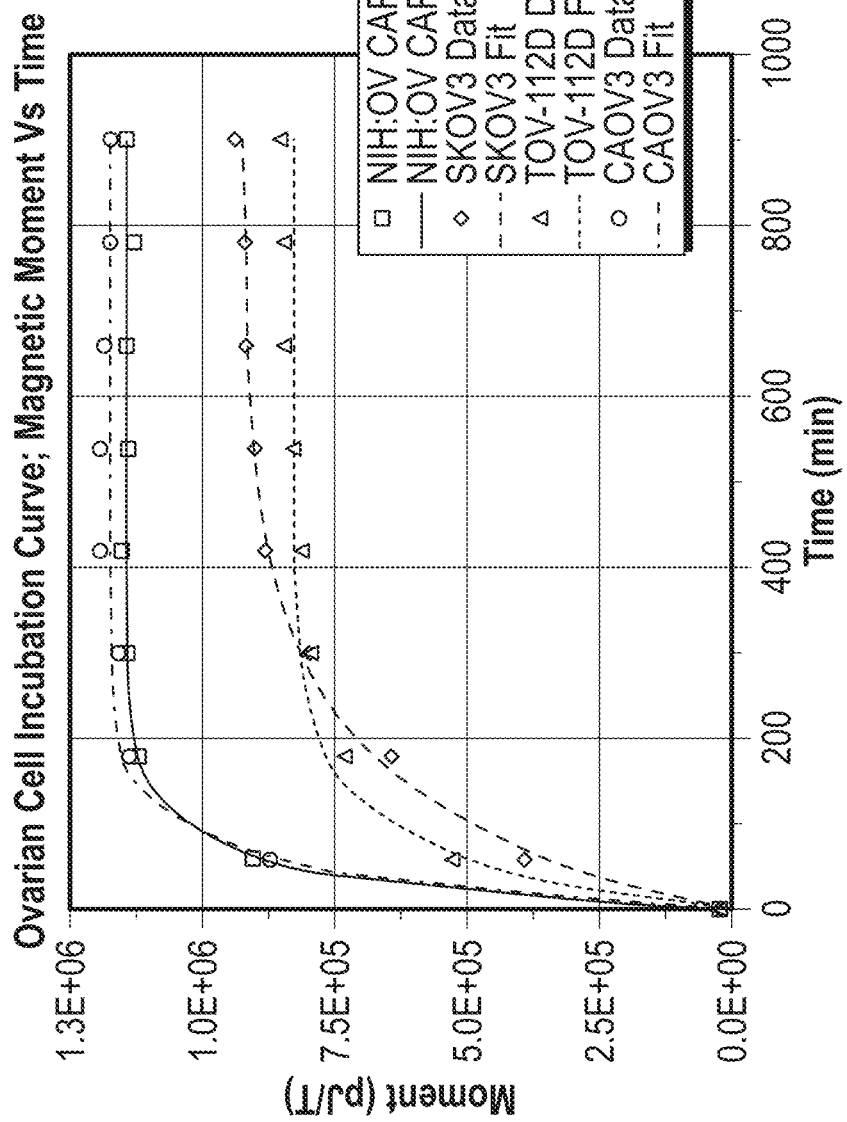
FIG. 8 illustrates the results of an incubation measurement on four different ovarian cell lines with the antibody CA-125. The solid lines are theoretical fits to the data. The lower box gives the results of the fits including the ovarian cell line, the ratio of nanoparticle sites on the cells, the density of nanoparticles on the cells, the rate constant, the number of ovarian cells in the sample and the number of nanoparticles per cell as determined by the procedure shown in FIG. 7.

Examples of quantitative results are illustrated in FIG. 8 where ovarian cancer cells are incubated with Ab specific to ovarian cancer, the figure contains data obtained during the incubation of four ovarian cancer cell lines and the Ab CA-125. The solid lines are the results of fitting the data to the equations described above. The table at the bottom of the figure lists the parameters obtained by this fitting procedure for all four cell lines. Three million cells were used in each incubation study. Using the measured np+Ab density extracted from the fit, the relative specificity for the CA-125 Ab to each cell line is listed in column 2, the rate constant in column 4 and the number of np+Ab per cell listed in column 6. The ability to extract these numbers from the incubation data is an attribute of this invention and is not possible by other incubation process known to the inventor.

Figure 9:
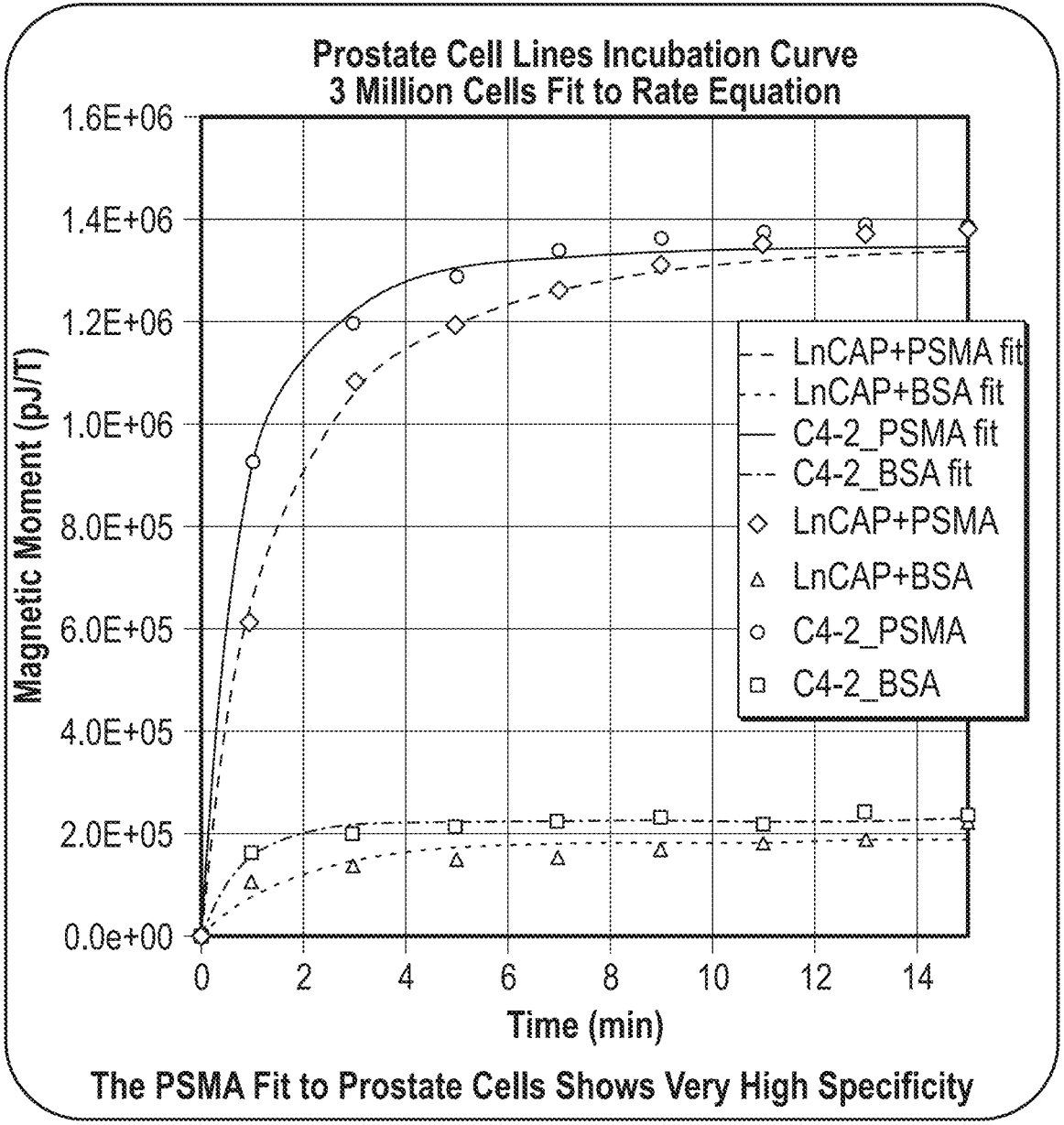
FIG. 9. Illustrates the results of an incubation measurement on two different prostate cell lines, LNCAP and C4-2 incubated with the prostate antibody PSMA and a non-specific chemical agent BSA to show the specificity of antibodies. The lines are fits to the data. The table contains all the input parameters necessary to obtain the fits and the resulting nanoparticles/cell and the rate of incubation.

The embodiment of this invention to provide detailed information from the incubation of cells and molecules is further illustrated in FIG. 9. In these studies, two prostate cell lines were used, LnCAP and C4-2, incubated with two different molecules, PSMA an Ab for prostate cancer and BSA (bovine serum albumin a protein). The solid lines fitting the data are from the equations described in FIG. 7. The table at the right outlines the complete procedure used in determining quantitative results using measurements of the number of np+Ab in the solution used for incubation, number of cells used, and the values used for weight and magnetic moment for an individual np. These latter results are obtained independently; they are applicable to all incubation experiments using the same np. This embodiment of this invention also shows, the capability for this invention to use molecules other than Ab, in this case the BSA molecule, to measure the quantity of such molecules to bind to the cells.

Figure 10:
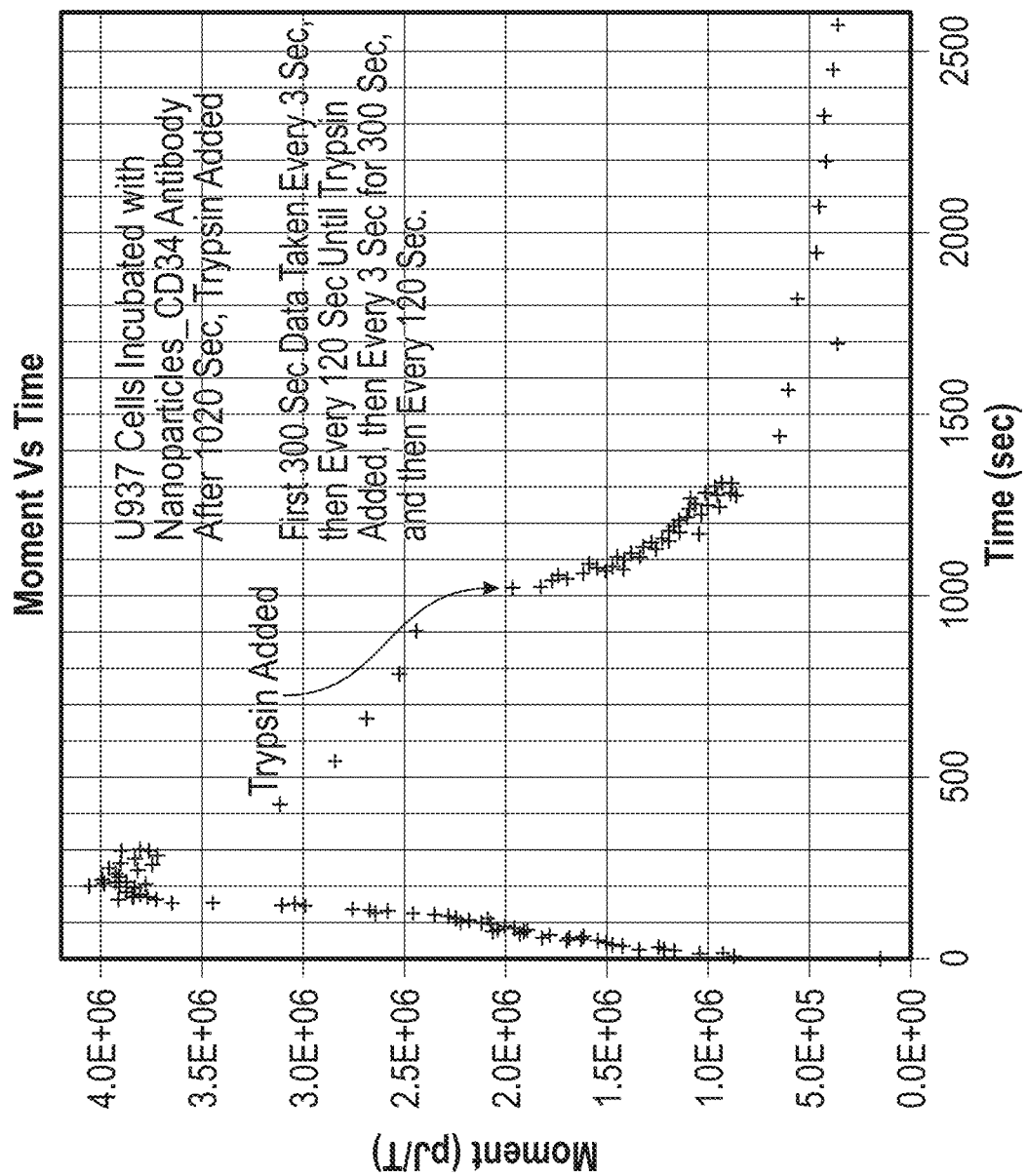
FIG. 10 illustrates the results of an incubation measurement of a leukemia cell line, U937, with an antibody for leukemia, (CD34) with the measured magnetic moment of the sample plotted against time. At 1020 seconds, a molecule trypsin was added during the incubation period.

In another embodiment of this invention, the effects of adding molecules that change the binding of molecules to cancer cells can be determined. In FIG. 10, leukemia cells (U937) are being incubated with np conjugated to the Ab, CD34. During the incubation the molecule trypsin is added. Trypsin acts to strip Ab from cells, unbinding the np+Ab from the cells resulting in their removal from contributing to the observed magnetic moment of the assembly. The result of adding this molecule is a sharp drop in signal following the addition of trypsin. This observation demonstrates that this invention may be used to examine the direct effect of various molecules on cells, such as chemotherapy on cancer cells.

FIG. 10 also shows the flexibility of this invention in measuring different aspects of incubation under different conditions. In these data the SPMR system was pulsed initially every 3 seconds until three hundred seconds to study the fine details of the incubation process. It was then pulsed every two minutes until one thousand seconds where the chemical trypsin was added. Following this it was pulsed every three seconds for three hundred more seconds, and then every two minutes until 2500 seconds were reached.

Figure 11:
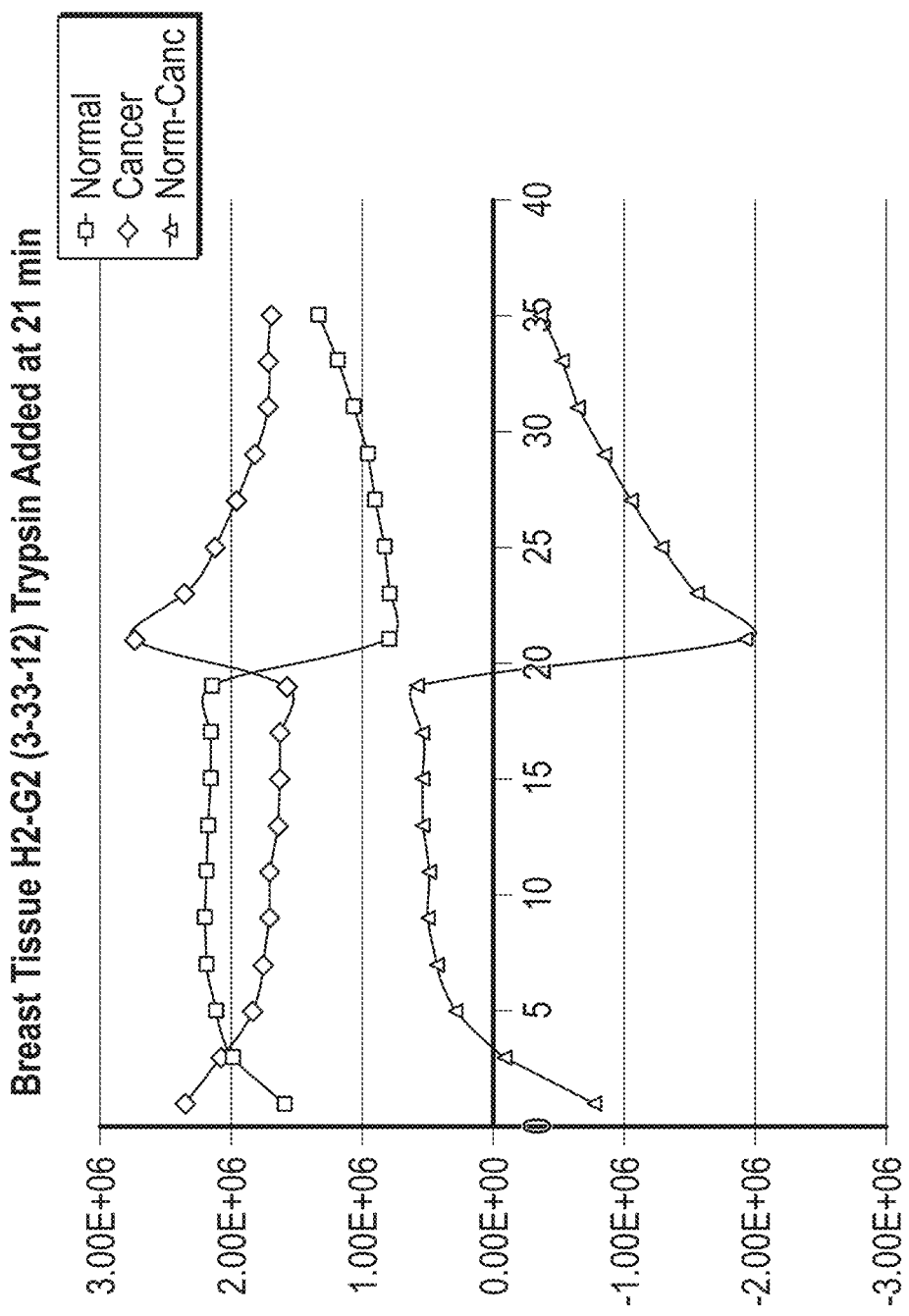
FIG. 11 illustrates the measurement of the magnetic moment versus time of two breast tissue samples previously soaked in a solution of Her2 antibodies plus nanoparticles where the vertical axis is the measured magnetic moment of the sample and the horizontal axis is time in minutes. The tissue samples obtained from the National Cancer Institute were from human patients following breast cancer surgery. At twenty-one minutes trypsin was added.

In another embodiment of this invention, tissue and biopsy samples may be examined for the presence of cancer cells by incubated them with molecules conjugated to supermagnetic np. FIG. 11 contains incubation from using fixed breast cancer tissue obtained during surgery (The samples were supplied by the National Cancer Institute for research studies). Results shown are for two examples of such tissue. For twenty minutes the tissue was incubated with the antibody Her2 conjugated with np followed by the molecule trypsin being added to examine the effect of trypsin on the np+Ab on the cells. The resulting tissue samples reacted in opposite ways to the trypsin, the lower curve is the difference between the two samples revealing the large effect of the molecule added. Results such as this in real time are impossible with biochemical incubation methods. Details of the tissue samples were not available at the time of these measurements limiting the interpretation of the data.

The invention described here utilizes a single magnetometer to measure the magnetic dipole fields emitted by the sample under incubation, multiple sensors are not required as the location of the source is known, and mapping is not needed to determine the magnetic moment of the sample. For optimal performance a magnetic sensor capable of observing $1 \times 10^4$ pJ/T magnetic dipole moment is desirable. The dipolar magnetic field is a function of the distance between sample to sensor according to the inverse cube root of the distance. A sample containing a source $1 \times 10^4$ pJ/T with the superparamagnetic np used in the above incubation examples produces a magnetic field of $2.0 \times 10^3$ pT/√Hz at one cm, $2.3 \times 10^2$ pT/√Hz at two cm, 6.4 pT/√Hz at 3 cm and 0.25 pT/√Hz at four cm. As an example of magnetic fields produced during an incubation measurement the lowest magnetic moment measured during the incubation of prostate cells in FIG. 9 was ~$1 \times 10^5$ pJ/T for three million cells, a typical amount used during incubation studies. The magnetic field at two cm from this source would be $2.3 \times 10^3$ pT/√Hz or ~$8.0 \times 10^2$ pT/√Hz. The embodiment of this invention as shown in FIG. 1 is designed to minimize sensor to source distance whereas this distance is determined by the geometry of the system in FIG. 2 to approximately four cm. A choice of sensors is possible in the present invention because of the capability of enclosing the SPMR measurement system in a magnetically shielded enclosure. This is not economically possible in the system shown in FIG. 2 because of its large size which makes the system of FIG. 2 not suitable to be portable via hand carry.

Figure 12A:
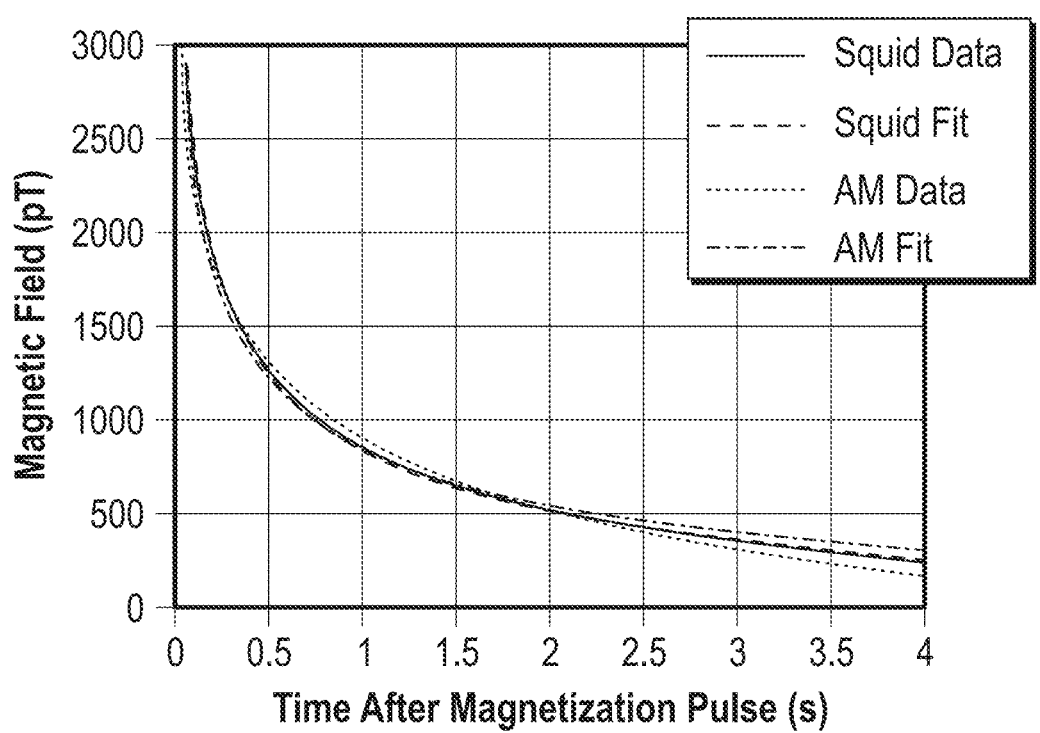
FIG. 12A-B is a schematic of an optical magnetometer that has been used to measure the incubation of cancer cells with np+Ab.
Figure 12B:
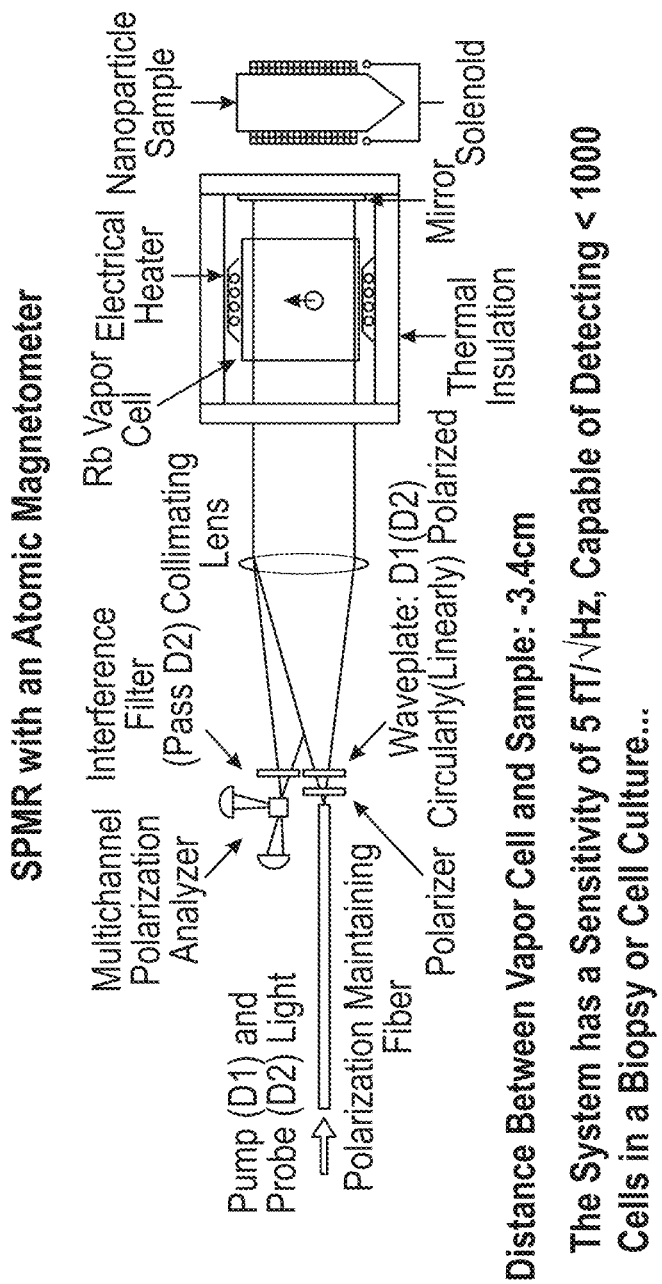

In one embodiment of this invention, a magnetometer capable of the necessary sensitivity is shown in FIG. 12A-B. This atomic magnetometer (Johnson et al) has been used in SPMR measurements of incubated cells by the author of this invention as shown in the figure. It is capable of sensitivities of $5 \times 10^{-3}$ pT/√Hz. This sensor system may be fit into the sensor tube as shown in FIG. 1. The fiber optics required for laser beams and pickup signals are extracted from the top of the sensor tube.

Figure 13A:
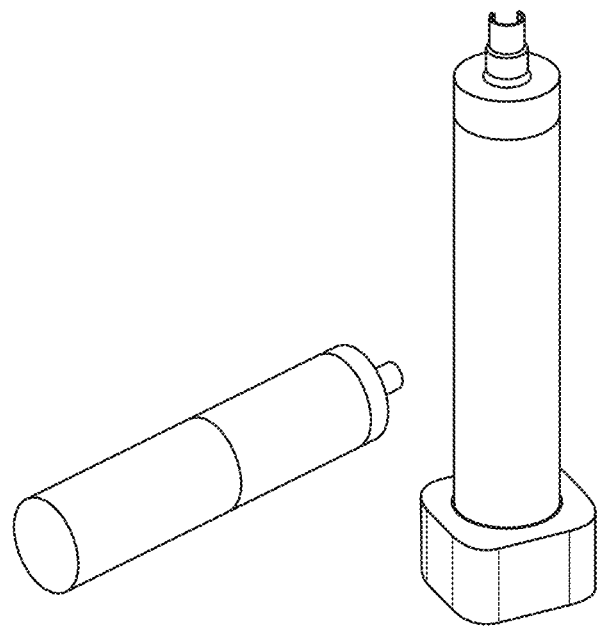
FIG. 13A-B contains examples of two magnetic sensors that could be used with this invention: (1) a HTC SQUID sensor operating at liquid nitrogen temperature, (2) an atomic magnetometer.
Figure 13B:
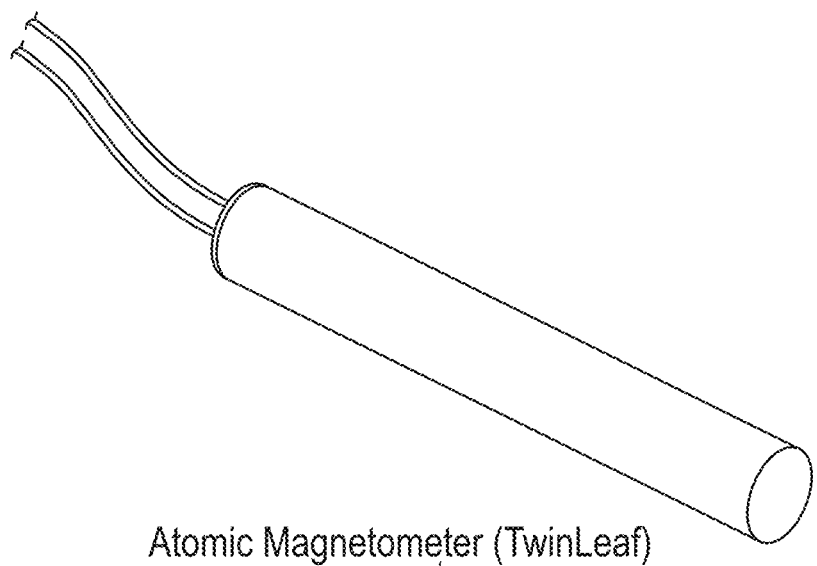

In other embodiments of the invention, flexibility in magnetic sensor type and design is an attribute as the system does not require the ultra-sensitive low temperature SQUIDs that use liquid helium. It is possible to use a variety of other magnetic sensors depending on the need for sensitivity and the existing environmental background noise. FIG. 13A-B contains two examples of commercial magnetic sensors whose sensitivity exceeds the requirements of this invention for most applications. The author of this invention has experience with both high temperature and low temperature SQUID sensors including the construction of a high temperature SQUID sensor operating at liquid nitrogen temperature (Espy et al). The HTC SQUID option available from Tristan requires only liquid nitrogen to operate and is available as a gradiometer minimizing the need for shielding. A second option that is available commercially and would fit into the sensor insertion tube is the atomic magnetometer available from Twinleaf. Other options include fluxgate and magneto resistive sensors. Commercially available sensors of this type currently have limited sensitivity; however such sensors are being developed in laboratories with sensitivity exceeding the desired $10^2$ pT/√Hz. These are examples of numerous choices for sensors that satisfy the present invention's sensitivity requirements and do not require liquid helium.

In the current invention, reduction in environmental magnetic background is achieved by constructing the containment chamber of the device shown in FIG. 1 out of magnetic shielding such as mu-metal. The small stature of the device makes this a simple inexpensive option. It is not possible to use such shielding in the animal SPMR device shown in FIG. 2 resulting in environmental magnetic noise limiting its performance.

The preceding examples can be repeated with similar success by substituting the generically or specifically described reactants and/or operating conditions of this invention for those used in the preceding examples.

Note that in the specification and claims, "about" or "approximately" means within twenty percent (20%) of the numerical amount cited. All computer software disclosed herein may be embodied on any computer-readable medium (including combinations of mediums), including without limitation CD-ROMs, DVD-ROMs, hard drives (local or network storage device), USB keys, other removable drives, ROM, and firmware.

Although the invention has been described in detail with particular reference to these embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

REFERENCES CITED

| | | |
|---|---|---|
| 4,018,886 | April 1997 | Giaever |
| 4,442,404 | April 1984 | Bergmann |
| 4,590,922 | May 1986 | Calenoff |
| 4,675,286 | June 1987 | Gordon |
| 4,735,796 | April 1988 | Gordon |
| 4,829,984 | May 1989 | Gordon |
| 4,859,610 | August 1989 | Maggio |
| 4,950,221 | August 1990 | Gordon |
| 4,962,023 | October 1990 | Todd |
| 5,043,101 | August 1991 | Gordon |
| 5,384,109 | January 1995 | Klaveness et al |
| 5,496,534 | March 1996 | Klaveness et al |
| 5,506,500 | April 1996 | Krause et al |
| 5,735,279 | April 1998 | Klaveness et al |
| 5,735,279 | April 1998 | Klaveness et al |
| 5,759,793 | June 1998 | Schwartz |
| 5,827,478 | October 1998 | Carey |
| 5,921,244 | July 1999 | Chen |
| 5,928,535 | July 1999 | Reuss |
| 6,203,487 | March 2001 | Consigny |
| 6,203,487 | March 2001 | Consigny |
| 6,470,220 | October 2002 | Kraus |
| 6,485,985 | November 2002 | Weitschies |
| 6,739,342 | May 2004 | Fredriksson |
| 6,997,863 | February 2006 | Handy et al |
| 6,997,863 | February 2006 | Handy et al |
| 7,074,175 | July 2006 | Handy et al |
| 7,217,391 | May 2007 | Gjerdingen |
| 7,309,316 | December 2007 | Flynn |
| 7,452,662 | November 2008 | Dupuis |
| 7,459,145 | December 2008 | Bao |
| 7,662,632 | February 2010 | Kuppusamy |
| 7,906,345 | March 2011 | Wang |
| 8,060,179 | November 2011 | Flynn |
| 8,323,957 | December 2012 | Bartsch |
| 8,394,339 | March 2013 | Silverbrook |
| 8,447,379 | May 2013 | Flynn |
| 8,834,381 | February 2013 | Sillerud |
| 8,947,518 | February 2015 | Kiyota |
| 9,074,976 | July 2015 | Adolphi |
| 9,081,007 | July 2015 | Pollack |
| 9,095,270 | August 2015 | Flynn |
| 9,395,361 | July 2016 | Pamula |

| | | |
|---|---|---|
| 9,404,074 | August 2016 | Kiyota |
| 9,428,723 | August 2016 | Lee |
| 10/031,132 | July 2018 | Foppen |
| 10/233,481 | March 2019 | Marshall |

OTHER REFERENCES

Adolphi et al., Characterization of magnetite nanoparticles for SQUID-relaxometry and magnetic needle biopsy, Feb. 20, 2009, Journal of Magnetism and Magnetic Materials, vol. 321, Is. 10, p. 1459-1464. cited by applicant Y. R. Chemla H. L. Grossman, Y. Poon, McDermott, R. Stevens, M. D. Alper, and J. Clarke, "Ultrasensitive magnetic biosensor for homogeneous immunoassay" Proc Natl Acad Sci USA. Dec. 19, 2000; 97(26): 14268-14272, retrieved from URL: http://www.ncbi.nlm.nih.gov/pmc/articles/PMC18907/. cited by applicant.

Flynn, E. R. et al. A biomagnetic system for in vivo cancer imaging. Institute of Physics Publishing, Physics in Medicine and Biology. Phys. Med. Bio. 50 2005, 1273-1293. cited by applicant.

Flynn E R, Bryant, H C, Bergemann C, Larson R S, Lovato D, Sergatskov D A, *Use of a SQUID array to detect T-cells with magnetic nanoparticles in determining transplant rejection*, JMMM, 311 (2007) 429-435

Adolphi N L, Huber D L, Bryant H C, Monson T C, Fegan D L, Lim J K, Jaetao J E, Tessier T E, Lovato D M, Butler K S, Provencio P C, Hathaway H J, Majetich S A, Larson R S, and Flynn E R. *Characterization of Single-core Magnetite Nanoparticles for Magnetic Imaging by SQUID-relaxometry*, PMB 55 (2010) 5985 Cited by applicant Bryant, H. C., Adolphi, N. L., Huber, D. L., Danielle Fegan, D. L., Monson, T. C., Tessier, T. E., Flynn, E R, *Magnetic Properties of Nanoparticles Useful for SQUID Relaxometry in Biomedical Applications*, JMMM 2010 Cited by applicant Hathaway H J, Butler K S, Adolphi N A, Lovato D M, Belfont R, Fegan D L, Monson T C, Trujillo J E, Tessier T E, Bryant H C, Huber D L, Larson R S, Flynn E R, *A novel method for early detection of breast cancer using magnetic nanoparticles and ultra-sensitive magnetic field sensors*, Breast Cancer Research 13:R108 (2011) (online). Cited by applicant.

Adolphi N A, Butler K S, Lovato D M, Tessier T E, Trujillo J E, Hathaway H J, Fegan D M, Monson T C, Stevens T E, Huber D L, Ramu J, Milne M L, Conradi M S, Altobelli S A, Larson R S, Flynn E R, *Imaging of Her2-targeted magnetic nanoparticles for breast cancer detection*, comparison of SQUID-detected magnetic relaxometry and MRI, Contrast Media and Molecular Imaging 7 (3) 2012, 308-319 Cited by applicant Butler K S, Lovato D M, Adolphi N A, Belfont R, Fegan D M, Monson T C, Hathaway H J, Huber D L, Tessier T E, Bryant H C, Flynn E R, and Larson R S, *Development of antibody-tagged nanoparticles for noninvasive detection of transplant rejection using biomagnetic sensors*, submitted to Cell Transplantation (2012) Cited by applicant Johnson C, Adolphi N L, Butler K, Lovato D M, Larson R, Schwindt D D, Flynn E R, Biological Application of Magnetic Relaxometry with Atomic Magnetometer and SQUID Sensors, JMMM 324 (2012) 2613-2619

Jaetao J E, Butler K S, Adolphi N L, Lovato, D M, Bryant H C, Rabinowitz I, Winter S S, Tessier T E, Hathaway H J, Bergemann C, Flynn E R, and Larson R S, *Enhanced Leukemia Cell Detection Using a Novel Magnetic Needle and Nanoparticles*, Cancer Res 69 (21)2009, 8310-8316 cited by applicant Leyma P. De Haro, Todor Karaulanov, Erika C. Vreeland, Bill Anderson, Helen J. Hathaway, Dale L. Huber, Andrei N. Matlashov, Christopher P. Nettles, Andrew D. Price, Todd C. Monson and Edward R. Flynn, *Magnetic relaxometry as applied to sensitive cancer detection and localization*, Biomed. Eng.-Biomed. Tech. 2015; aop M. A. Espy, R. H. Kraus, Jr., E. R. Flynn, and A. Matlashov, Two methods for a first order hardware gradiometer using two high temperature superconducting quantum interference devices, Rev. Sci. Instrum., 123 (1998).

What is claimed is:

1. A device comprising:
    a measurement chamber formed of magnetically shielding metal;
    a sample holder;
    a plurality of magnetizing coils that when automatically pulsed by an appropriately programmed computer in communication therewith produce a uniform unidirectional magnetic field on a sample within the sample holder and in a direction perpendicular to the sensor face; and
    a single magnetic field sensor that receives instructions from the appropriately programed computer to measure a magnetic fields because of the localized geometry of source and sensor wherein the magnetic sensor is sensitive to about ≤800 pT/√Hz and operates in the absence of liquid helium cooling; and
    the appropriately programed computer having instructions for performing the steps of:
        pulsing a magnetizing field from the plurality of magnetizing coils for a period of time between an on state and off state;
        switching off the single magnetic field sensor prior to the period of time the uniform unidirectional magnetic field is in the on state; and
        turning on the single magnetic field sensor following the period of time the uniform unidirectional magnetic field is in the off state.

2. The device of claim 1 wherein the device is approximately 20 cm in diameter by 20 cm in height as determined by a size of the magnetizing coils and spacing for insertion of samples and magnetic sensor.

3. The device of claim 1 wherein the sample holder further comprises an insertion tube constructed of a same material as the chamber for additional magnetic shielding.

4. The device of claim 1 wherein a single magnetic field sensor tube protrudes from a top of the device assembly.

5. The device of claim 1 wherein the plurality of magnetizing coils are located above and below the sample holder containing a sample when the device is in use.

6. The device of claim 1 comprising a Helmholtz coil where each magnetizing coil is about ten cm in diameter and the distance between the two coils is about 5 cm producing a magnetic field at the center of about 75 Gauss (0.0075 T) when a current of about 5 A consuming a power of less than one hundred watts is produced through the coils.

7. The device of claim 1 wherein the magnetizing coils is aligned with the magnetic sensors that measure magnetic fields in the direction perpendicular to a sensor face of the magnetic sensor.

8. The device of claim 1 wherein the computer program instructions further comprise:

measuring a decaying of the magnetic field of the sample for a fixed interval of time;

calculating a magnetic dipole of the sample from the decaying of the magnetic field; and calculating an incubation result from a magnetic dipole magnitudes from the sample.

9. The device of claim 1 wherein the period of time that the magnetizing coils are pulsed in the on state is 0.75 sec at 75 Gauss magnetic pulse.

10. The device of claim 1 wherein the single magnetic field sensor is turned on within 40 millisecs following the off state of the uniform unidirectional magnetic field.

11. A method for measuring, with a device of claim 1, incubation of living cells with molecules attached to superparamagnetic nanoparticles consisting essentially of iron cores, the method comprising the steps of:

magnetizing the superparamagnetic nanoparticles with an external pulsed field;

measuring the time dependence of decaying magnetic fields of the superparamagnetic nanoparticles as they attach to the cells by a magnetic sensor; and extracting a number of attached superparamagnetic nanoparticles per cell and rate of incubation by mathematical analysis of the magnetic field emitted by the incubating cells versus time.

12. The method of claim 11 where the cells are cancer cells and the molecule is an antibody.

13. The method of claim 11 where the cells are tumor cells and the molecule is an antibody.

14. The method of claim 11 where the cells are blood cells and the molecule is an antibody.

15. The method of claim 11 where the cells are bone marrow cells and the molecule is an antibody.

16. The method of claim 11 where the cells are T-cells and the molecule is an antibody.

17. The method of claim 11 where a second molecule is added to change the incubation process.

18. The method of claim 11 where the cells are from a biopsy and the molecule is an antibody.

19. The method of claim 11 where the cells are from tissue taken from the body and the molecule is an antibody.

20. The method of claim 11 where the molecule is not an antibody.

21. The method of claim 11 to measure the specificity of an antibody for cells.

22. The method of claim 11 to measure the properties of superparamagnetic nanoparticles for magnetic relaxometry incubation.

* * * * *